United States Patent
Miles

(10) Patent No.: US 11,497,727 B2
(45) Date of Patent: Nov. 15, 2022

(54) SYSTEM AND METHOD FOR MAKING CANNABINOID NANOPARTICLE CARRIER COMPOSITION

(71) Applicant: Aaron Miles, McKinleyville, CA (US)

(72) Inventor: Aaron Miles, McKinleyville, CA (US)

( * ) Notice: Subject to any disclaimer, the term of this patent is extended or adjusted under 35 U.S.C. 154(b) by 306 days.

(21) Appl. No.: 16/946,838

(22) Filed: Jul. 8, 2020

(65) Prior Publication Data

US 2021/0008025 A1 Jan. 14, 2021

Related U.S. Application Data

(60) Provisional application No. 62/871,653, filed on Jul. 8, 2019.

(51) Int. Cl.
*A61K 31/352* (2006.01)
*A61K 31/05* (2006.01)
*A61K 9/107* (2006.01)

(52) U.S. Cl.
CPC .......... *A61K 31/352* (2013.01); *A61K 9/1075* (2013.01); *A61K 31/05* (2013.01)

(58) Field of Classification Search
CPC .................................................... A61K 31/352
USPC ........................................................ 514/454
See application file for complete search history.

(56) References Cited

PUBLICATIONS

Fathordoobady, Nature Research Scientific Reports (2021), 11(1), 72.*

* cited by examiner

*Primary Examiner* — Nizal S Chandrakumar

(57) ABSTRACT

A method of producing a cannabinoid nanoparticle carrier composition for administration to a human, including the steps of incorporating non-ionic surfactants with cannabinoid oils and lipids; inducing sonication for a predetermined period of time at a predetermined amplification with a ultrasonic liquid processor until completely integrated; dissolving ascorbic acid into a carrier fluid; combining in sequence the non-ionic surfactants, lipids, and cannabinoids with a carrier fluid consisting of distilled water and ascorbic acid; sonicating using an ultrasonic liquid processor at predetermined amplitude for a predetermined period of time at a controlled temperature.

10 Claims, No Drawings

SYSTEM AND METHOD FOR MAKING CANNABINOID NANOPARTICLE CARRIER COMPOSITION

CROSS REFERENCES TO RELATED APPLICATIONS

The present application claims the benefit of the filing date of U.S. Provisional Patent Application Ser. No. 62/871,653, filed Jul. 8, 2019, which application is incorporated in its entirety by reference herein.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

Field of the Invention

The present invention relates most generally to water soluble emulsions, and more particularly to emulsions containing water-immiscible cannabinoids, and still more particularly to a cannabinoid nanoparticle carrier composition suitable for therapeutic use.

Background Discussion

Cannabinoid emulsions are known, as are lipid based cannabinoid compositions. U.S. Pat. No. 10,028,919, to Kaufman, describes one such composition. And U.S. Pat. App. Ser. No. 2009/01810890, by Kottayil, describes methods for making an effective amount of a cannabinoid in a semi-aqueous solution buffered to a pH of 5-10.

However, these two patent publications, while reflecting the current state of the art of which the present inventor is aware, do not teach or disclose, suggest, show, or otherwise render obvious, either singly or when considered in combination, the inventive method described herein. Specifically, the cited references teach cannabinoid products extremely involved manufacturing processes. The present invention, by contrast, is a simple method of formulating a water soluble, lipid-based cannabinoid nanoparticle carrier composition which includes the use of emulsifiers (surface active agents) and sonication or ultrasonic processes to render a cannabinoid nanoemulsion.

BRIEF SUMMARY OF THE INVENTION

The present invention is a system and method for extracting and making cannabinoid emulsifications, as well as the product produced thereby.

In its most essential aspect, the present invention is a method of producing a cannabinoid nanoparticle carrier composition for administration to a human, including the steps of: (a) mixing non-ionic surfactants with cannabinoid oils and lipids in a mixing vessel; (b) processing the mixture made in step (a) using sonication for a predetermined time at a predetermined amplification until completely processed and substantially all of the cannabinoid oils are reduced to nanoparticle size in a cannabinoid oil complex (COC); (c) dissolving an acid in a carrier fluid to make an acidic carrier fluid solution; (d) mixing the COC made in steps (a) and (b) with the acidic carrier fluid solution made in step (c); and (e) sonicating the mixture made in step (d) using an ultrasonic liquid processor operated at a predetermined amplitude for a predetermined time at a controlled temperature.

In embodiments, the foregoing method may include a first mixing step involving mixing non-ionic surfactants with cannabinoid oils and lipids in relative proportions of 5:9:9 by weight.

In further embodiments, the mixing step includes mixing approximately 5000 mg of non-ionic surfactants with approximately 9000 mg of cannabinoid oils, and approximately 9000 mg lipids.

In still further embodiments, the first sonication step includes inducing sonication for approximately 90 seconds at 60% amplification.

Still other embodiments include sonication using an ultrasonic liquid processor.

In other embodiments, step of making an acidic carrier fluid solution entails dissolving approximately 1000 mg of ascorbic acid in a carrier fluid, such as distilled water, glycerides, lipids, and mixtures thereof.

Other embodiments can include making an acidic carrier fluid solution consisting of approximately 76 g distilled water and 1000 mg ascorbic acid.

In embodiments, the second sonication step can include sonicating at 60% using ultrasonic liquid processor. This embodiment may further include sonicating at 60% amplitude, and still further it may include continuing the sonication a predetermined time, e.g., approximately 5 minutes at a constant temperature, e.g., 24 C.

As will be appreciated from the foregoing, in each of the embodiments above, the method of the present invention produces a cannabinoid-containing nanoparticle carrier composition.

BRIEF DESCRIPTION OF SEVERAL VIEWS OF THE DRAWINGS

Not applicable. The present invention, both as a process and as a product by process, may be understood without reference to illustrations.

DETAILED DESCRIPTION OF THE INVENTION

The inventive is directed to a method of producing a cannabinoid nanoparticle carrier composition for therapeutic use, wherein the cannabinoid carrier composition improves bioavailabilty of the cannabinoids in the composition, as well as improves accurate dosing, due to the more precise measure. Various means of administration may be employed, including intraoral administration, peroral administration, transdermal administration, or intranasal administration. An exemplary composition produced by the inventive method may contain: (1) firstly, 1-15% Cannabinoids: Comprising of at least one of the Phytocannabinoids found in cannabis that include delta-9-Tetrahydrocannabinol (THC), Cannabidiol (CBD), Cannabinol (CBN) Cannabigerol (CBG}, Cannabigerol {CBG), Cannabichromene (CBC), Cannabicyclol (CBL), Canabivarol (CBV), Tetrahydrocannabiverin (THCV), Cannabidivarin (CBDV), Cannabichromevarin (CBCV, Cannabigerol Monoethyi ether (CBGM); (2) secondly, 1-20% Lipids (medium chain triglycerides, glycerides, hemps seed oil, safflower oil, sunflower oil, olive oil, etc.); and (3) thirdly, 1-10% pharmaceutical food grade surfactants (SpanLipophilic), (Tween-hydrophilic, e.g, as Tween 80, E433), to function as emulsifiers. They may be used independently or in any combination of the following: 20, sorbitan monopalmitate; Span® 40, sorbitan monopalmitate; Span® 60, sorbitan monostearate; and Span 80, sorbitan monooleate). Tween® are hydrophilic, Span® are lipophilic. [TWEEN is a registered trademark of Croda Americas LLC of Bridgewater, N.J.; SPAN is a registered trademark of Merck KGaA of Darmstadt, Germany.]

An exemplary non-limiting method of making the inventive composition entails the following steps, wherein the steps are non-limiting in the relative proportions of the composition components and recited amounts are understood to be close approximations:

(1) Mixing 5000 mg of non-ionic surfactants with 9000 mg of cannabinoid oils, and 9000 mg lipids in a mixing vessel, e.g., a 200 ml beaker.

(2) Inducing sonication for 90 seconds at 60% amplification with a ultrasonic liquid processor until completely integrated.

(3) Dissolving 1000 mg of ascorbic acid into a carrier fluid selected from the group consisting of distilled water, glycerides, lipids, or a mixture thereof.

(4) Combining in sequence the non-ionic surfactants, lipids, and cannabanoid oil complex (COC) with the carrier fluid/ascorbic acid solution, which may consist of 76 g distilled water and 1000 mg ascorbic acid.

(5) Sonicating at 60% using ultrasonic liquid processor at 60% amplitude for 5 minutes, at a constant 24 c temperature. The final weight of this exemplary nanoemulsion is 11.0 g at 100 ml.

The following protocol applies: The ingredients are processed using a single or dual phase process utilizing sonication or ultrasonic processes for a determined period of time to produce a water-soluble nanoemulsion.

The formula consists of: (a) non-ionic TWEEN® or SPAN® pharmaceutical food grade surfactants in specific combination or percentages to acquire 1-10% total surfactants; (b) refined olive oil 1 to 20%; (c) ascorbic acid 0.01-3%; (d) THC or CBD cannabinoids in any form of hemp or any classification form in any combination, whether concentration quantity or potency, 1-15%, in specific combinations; and (e) to achieve 100% of total formula weight or volume, the remaining ingredient is distilled water alone.

Importantly, the inventive composition does not include lecithin or lecithin-based essential phospholipids. Rather, it involves the use of sonication or ultrasonic processing of the water-immiscible mixture to achieve the nanoemulsion.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the claims included herein.

What is claimed as invention is:

1. A method of producing a cannabinoid nanoparticle carrier composition for administration to a human, comprising:
    (a) mixing non-ionic surfactants with cannabinoid oils and lipids in a mixing vessel, wherein the non-ionic surfactants, cannabinoid oils, and lipids, respectively, are mixed in relative proportions of 5:9:9 by weight of the total formula weight;
    (b) processing the mixture made in step (a) using sonication until completely processed and substantially all of the cannabinoid oils are reduced to nanoparticle size in a cannabinoid oil complex (COC);
    (c) dissolving ascorbic acid in a carrier fluid to make an acidic carrier fluid solution, wherein the ascorbic acid is in a relative amount of 0.01-3% by weight of the total formula weight;
    (d) mixing the COC made in steps (a) and (b) with the acidic carrier fluid solution made in step (c); and
    (e) sonicating the mixture made in step (d) using an ultrasonic liquid processor until substantially all of the cannabinoid oils are reduced to nanoparticle size in a cannabinoid oil composition.

2. The method of claim 1, wherein said step (a) mixing step comprises mixing approximately 5000 mg of non-ionic surfactants with approximately 9000 mg of cannabinoid oils, and approximately 9000 mg lipids.

3. The method of claim 1, wherein said step (b) processing step comprises inducing sonication for approximately 90 seconds at 60% amplification.

4. The method of claim 3, wherein said step (b) processing step involves using an ultrasonic liquid processor.

5. The method of claim 1, wherein said carrier fluid is selected from the group consisting of distilled water, glycerides, and lipids, and mixtures thereof.

6. The method of claim 5, wherein the acidic carrier fluid solution comprises approximately 76 g distilled water and 1 g (1000 mg) ascorbic acid.

7. The method of claim 6, wherein step (e) involves sonicating at 60% using ultrasonic liquid processor.

8. The method of claim 7, wherein the sonication of step (e) is conducted at 60% amplitude.

9. The method of claim 8, wherein the sonication of step (e) is continued for approximately 5 minutes.

10. The method of claim 9, wherein the sonication is carried out at a constant temperature.

* * * * *